(12) United States Patent
Fourcault et al.

(10) Patent No.: US 7,708,738 B2
(45) Date of Patent: May 4, 2010

(54) SELF-BORING AND SELF-TAPPING SCREW FOR OSTEOSYNTHESIS AND COMPRESSION

(75) Inventors: Eric Stéphane Fourcault, Lyons (FR); Theo Jan Maria Knevels, Grimbergen (BE); Jean-Christophe Alain Giet, Lyons (FR); Bertrand Xavier François Gauneau, Lyons (FR)

(73) Assignee: Newdeal S.A., Vienne (FR)

( * ) Notice: Subject to any disclaimer, the term of this patent is extended or adjusted under 35 U.S.C. 154(b) by 648 days.

(21) Appl. No.: 10/614,496

(22) Filed: Jul. 7, 2003

(65) Prior Publication Data

US 2004/0068261 A1    Apr. 8, 2004

(30) Foreign Application Priority Data

Jul. 5, 2002    (FR) .................................. 02 08589

(51) Int. Cl.
*A61B 17/56*    (2006.01)

(52) U.S. Cl. ........................... 606/67; 606/916; 606/304

(58) Field of Classification Search .................... 606/73, 606/72, 71, 70, 232, 67, 916, 304; 411/187, 411/389, 397, 395, 413; 433/173, 174, 225
See application file for complete search history.

(56) References Cited

U.S. PATENT DOCUMENTS

| 38,119 | A | * | 4/1863 | Morse ......................... 408/230 |
| 4,697,969 | A | * | 10/1987 | Sparkes .................... 411/387.7 |
| 4,871,313 | A | * | 10/1989 | Maillefer .................... 433/225 |
| 4,978,350 | A | | 12/1990 | Wagenknecht ................ 606/72 |
| 5,102,421 | A | * | 4/1992 | Anspach, Jr. ................. 606/232 |
| 5,897,319 | A | * | 4/1999 | Wagner et al. ............... 433/174 |
| 6,306,140 | B1 | * | 10/2001 | Siddiqui ....................... 606/73 |
| 6,319,254 | B1 | | 11/2001 | Giet et al. ...................... 606/73 |
| 6,398,785 | B2 | * | 6/2002 | Carchidi et al. ............... 606/73 |
| 6,402,757 | B1 | * | 6/2002 | Moore et al. .................. 606/80 |
| 6,604,945 | B1 | * | 8/2003 | Jones ......................... 433/173 |

FOREIGN PATENT DOCUMENTS

| EP | 0 856 293 A1 | 8/1998 | |
| EP | 1 145 691 A | 10/2001 | |
| FR | EP0856293 | * 8/1998 | .................. 606/67 |
| WO | 97/25939 | 7/1997 | |

* cited by examiner

*Primary Examiner*—Pedro Philogene
(74) *Attorney, Agent, or Firm*—Thomas, Kayden, Horstemeyer & Risley, LLP

(57) ABSTRACT

The invention provides an osteosynthesis and compression screw that is self-boring and self-tapping for the purpose of coaptation of small bone fragments. The screw comprises:
  a proximal portion formed by a screw head provided with an outside thread;
  an intermediate portion having no thread; and
  a distal portion provided with an outside thread.
Wherein:
  each of the screw head and the distal portion includes at least one groove, firstly extending over the entire axial length of its thread, and secondly being formed through each thread in such a manner to form tapping means; and
  the terminal zone of the distal portion is provided with preparation means for preparing a housing in the bone fragments for receiving the intermediate and distal portions of the screw.

19 Claims, 1 Drawing Sheet

SELF-BORING AND SELF-TAPPING SCREW FOR OSTEOSYNTHESIS AND COMPRESSION

CROSS REFERENCE TO RELATED APPLICATIONS

This application claims priority to a French Application No. 02 08589, filed Jul. 5, 2002.

FIELD OF THE INVENTION

The present invention relates to the technical field of surgical screws, and in particular to osteosynthesis screws for joining together and compressing two bone fragments in order to achieve rapid osteosynthesis with the formation of bone callus, the present invention applying more particularly to joining together small bone fragments such as those of the phalanges of the toes or the fingers.

The present invention relates to an osteosynthesis and compression screw for coaptation of small bone fragments, the screw being formed by a single longitudinal body, and comprising:
- a proximal portion formed by a screw head provided with an outside thread, said proximal portion being of diameter greater than the diameter of the remainder of the screw;
- an intermediate portion having no thread; and
- a distal portion provided with an outside thread.

BACKGROUND OF THE INVENTION

When dealing with broken bone fragments of small size, such as those of the phalanges or the toes, the small size of the bones or bone fragments concerned poses difficult problems to be solved by the practitioner in charge of reducing the fracture and then putting the bones into place with sufficient compression to ensure that the fracture is properly resorbed.

In order to ensure rapid osteosynthesis between two bone fragments, leading specifically to the rapid formation of a high quality bone callus enabling a rapid return to normal function, it is necessary for two small bone fragments to be positioned and fixed relative to each other with relative longitudinal compression being established between the two bone fragments.

Clearly, given the very small size of the bone fragments concerned, and the correspondingly small size of the osteosynthesis screws used, it is difficult to establish longitudinal compression between the two bone fragments concerned.

It is particularly important and difficult to master this type of surgical act, given that the manipulations imposed by the small size of the bones and the screws are fiddly, and given that the small bone fragments need to be positioned relative to one another and compressed and put into final position with very great precision since the purpose is to restore total mobility functions, such as handling functions or walking, in particular when dealing with bones of the hand or of the foot.

It is thus already known to use staples that are put into place directly on the two bone fragments to be joined together. Such a technique is poorly adapted to the type of surgery under consideration insofar as putting staples into place relative to the pieces of bone does not make it certain that the bone fragments to be joined together are properly positioned. In practice, it is not possible with staples to obtain fixing and compression.

Proposals have already been made to use osteosynthesis screws of the kind used for coaptation of bones of large size and suitable not only for joining bones together, but also for performing the additional function of applying longitudinal compression.

Thus, proposals have already been made to use an osteosynthesis and compression screw comprising a proximal portion formed by a screw head provided with an outside thread and presenting a diameter greater than that of the remainder of the screw. The screw presents an intermediate portion without any thread in order to improve relative sliding between the bone fragments for joining together while the screw is being screwed in, and said intermediate portion is followed by a distal portion which is also provided with an outside thread.

Such screws improve surgical operating conditions greatly because of the improve ease with which they can be put into place.

Nevertheless, such screws still suffer from drawbacks associated in particular with a certain number of additional actions that the surgeon needs to perform such as prior drilling of a hole in order to ensure that the threads of the screw hold strongly both in the distal portion and in the proximal portion having the head of larger diameter. This increases the number of actions the surgeon needs to perform and therefore increases the duration of the operation.

Considerable improvements have been provided to screws of this type but they relate essentially to increasing the compression ability of such screws, for example by incorporating a two-start distal thread, without taking account of total time required for surgery but while maintaining excellent holding strength and compression properties.

Conventional self-boring and self-tapping surgical screws are also known, with the tapping portion of such a prior screw nevertheless being restricted to the distal portion thereof. Screws known in the prior art possess a screw head that is not threaded and that must specifically be embedded in the bone by previously making a suitable recess using a special tool. Such screws thus require an additional tool to be used which implies an additional act leading to increased manipulation, to additional risk of accidents or faulty installation, and, in all, lengthening the time required for surgery.

OBJECTS AND SUMMARY OF THE INVENTION

The present invention consequently seeks to remedy the various drawbacks outlined above and to propose a novel osteosynthesis and compression screw for coaptation of small bone fragments, which screw is self-boring and self-tapping so as to simplify installation thereof and so as to enable installation to be controlled as well as possible.

Another object of the invention is to propose a novel osteosynthesis screw which is not only self-boring and self-tapping, but which also presents excellent strength properties.

Another object of the invention is to propose a novel osteosynthesis screw presenting excellent tapping properties while also being particularly well balanced geometrically.

Another object of the invention is to propose a novel osteosynthesis screw presenting excellent compression properties while being particularly well balanced mechanically.

The objects given to the invention are achieved by means of an osteosynthesis and compression screw for coaptation of small bone fragments, the screw being formed by a single longitudinal body having a longitudinal axis, and comprising:
- a proximal portion formed by a screw head provided with an outside thread, said proximal portion being of diameter greater than the diameter of the remainder of the screw;
- an intermediate portion having no thread; and
- a distal portion provided with an outside thread;

wherein:
  each of the screw head and the distal portion includes at least one groove, firstly extending over the entire axial length of its thread, and secondly being formed through each thread in such a manner to form tapping means; and the terminal zone of the distal portion is provided with preparation means for preparing a housing in the bone fragments for receiving the intermediate and distal portions of the screw.

BRIEF DESCRIPTION OF THE DRAWING

Other advantages of the invention are explained in greater detail in the description below, to be read with the help of the accompanying drawing provided purely for non-limiting explanatory purposes, and in which.

MORE DETAILED DESCRIPTION

Figure 1:
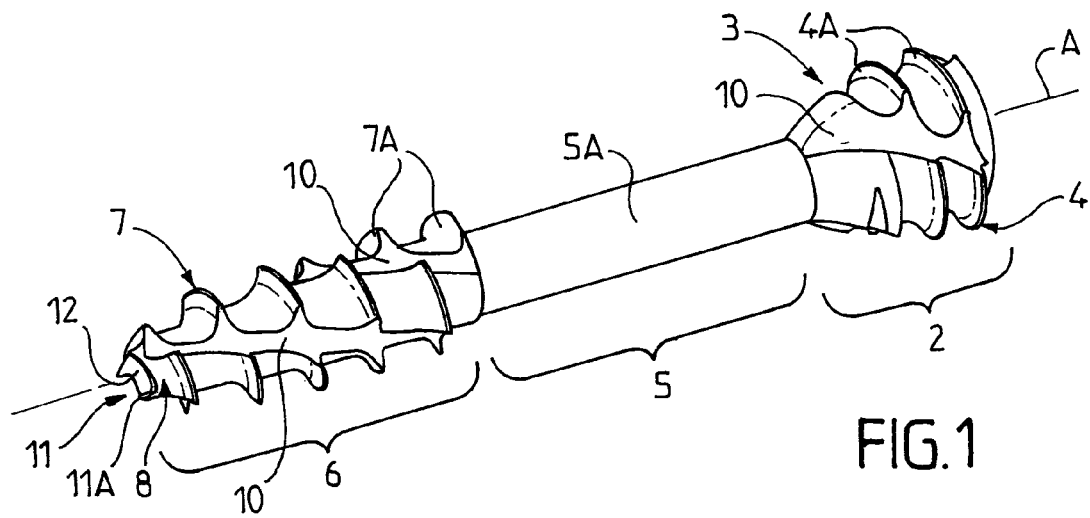
FIGS. 1 and 2 are general perspective views showing an embodiment of an osteosynthesis and compression screw in accordance with the invention.
Figure 2:
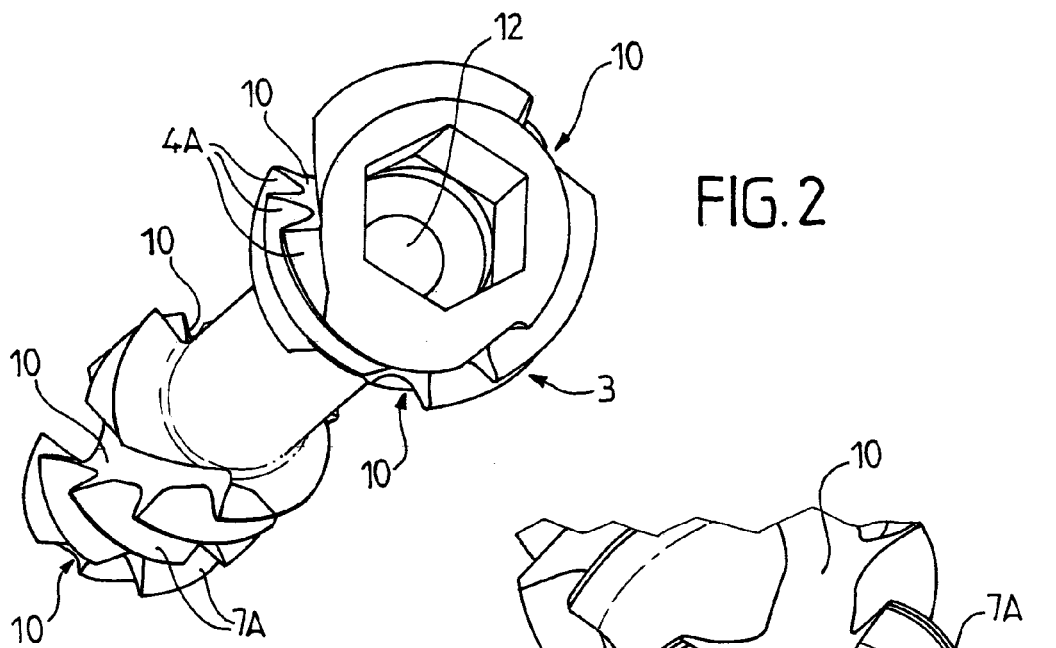
Figure 3:
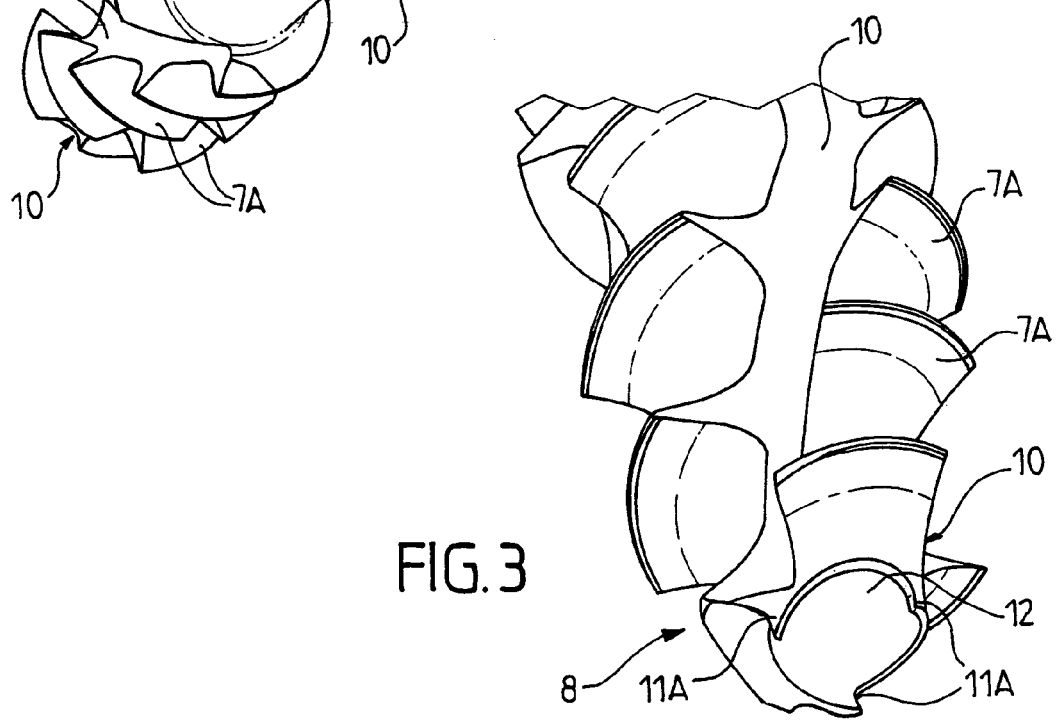
FIG. 3 is a fragmentary perspective view showing the shape of the distal portion of the screw in accordance with the invention.

The osteosynthesis and compression screw shown in the figures is for joining together or "coaptation" of two small bone fragments, and in particular in its preferred application, two phalanges of the foot or the hand that have been fractured.

The osteosynthesis and compression screw of the invention is made from a biocompatible metal material and is formed by a single elongate body presenting a longitudinal axis A defining an axis of revolution.

As shown in the figures, the osteosynthesis screw comprises a proximal portion 2 formed by a screw head 3 provided with an outside thread 4 comprising a series of helical threads 4A, said proximal portion 2 being of diameter D greater than the diameter of the remainder of the screw.

Thereafter, the osteosynthesis screw of the invention has an intermediate portion 5 that is not threaded, advantageously being in the form of a substantially cylindrical portion 5A that is smooth and of constant diameter.

The end of the intermediate portion 5 is extended by the distal portion 6 of the osteosynthesis screw, said distal portion being provided with an outside thread 7 extending helically, having individual threads 7A all the way to the terminal zone 8 of said distal portion 6.

In the invention, each of the screw head 3 and the distal portion 6 comprises at least one groove 10 extending substantially longitudinally relative to the general direction given by the longitudinal axis A over the full axial length of each thread 4, 7 and regardless of the shape of the groove 10, for example regardless of whether it is longitudinal or advantageously helical, said groove extending across each thread 4, 7, i.e. occupying the full height of each thread 4A, 7A so as to form tapping means of the screw. The screw of the invention thus comprises at least one pair of grooves 10 for performing tapping, both in the distal portion and in the proximal portion.

In the invention, the osteosynthesis screw of the invention also comprises, at the terminal zone 8 of the distal portion 6, means 11 for preparing a housing in the bone fragments for subsequently receiving the distal portion 6 and the intermediate portion 5 of said screw.

Advantageously, the compression effect is obtained by making the screw so that its proximal portion 2 has a thread at a pitch that is smaller than that of the thread of the distal portion 6.

Because of the technical means implemented in this way, the osteosynthesis screw of the invention serves not only to compress axially two bone fragments that are to be joined together by means of its two outside threads 4 and 7 in combination with the intermediate portion 5 whose smooth appearance allows the two bone fragments to slide towards each other, but also performs a self-boring action due to the preparation means 11, and above all it provides simultaneous self-tapping actions both at the head end of the screw and at its distal end. This design feature makes it possible to avoid prior drilling or recess forming using a special instrument, thereby reducing the total time required for surgery while also reducing the risk of faulty positioning since installing the screw and establishing compression is performed as a single action.

As shown in the figures, said at least one groove 10 present both in the head of the screw 3 and in its distal portion 6 is advantageously of helical shape and has the same geometrical orientation relative to the longitudinal axis A both in the vicinity of the head 3 and in the distal portion 6. The helical aspect of the grooves 10 may be more or less marked depending on the size and the shape of the screw, without that going beyond the ambit of the invention. The geometrical orientation of the screw may be specified by defining its obliqueness or angular orientation relative to the longitudinal axis A of the screw. The obliqueness of each groove 10 preferably lies in the range 20° to 40°, and more preferably is about 25°. Advantageously, the grooves 10 in the screw head 3 and in the distal portion 6 have the same obliqueness.

Naturally, in a variant, the pair or pairs of grooves 10 may be substantially longitudinal, i.e. they may extend substantially parallel to the longitudinal axis A, without thereby going beyond the ambit of the invention.

The depth of each groove 10 may be constant and equal between the grooves in the screw head 3 and in the distal portion 6.

Nevertheless, and advantageously, the depth of the grooves 10 varies regularly going from the start towards the finish of each groove, the "beginning" of each groove 10 in the meaning of the invention being, by definition, the end beginning in the most proximal portion of the screw head 3 or the distal portion 6. Thus, in the invention, the depth of each groove 10 increases going towards the more distal portion of the screw head 3 or of the distal portion 6. Thus, each groove 10 extends more and more deeply into each thread starting from the screw head 3 and going towards the distal portion 6, i.e. towards the terminal zone 8.

This feature, which means that the depth of the groove 10 is not constant relative to the longitudinal axis A of the screw, serves to increase the general strength of the screw, in particular in twisting, by significantly reducing the loss of material relative to said longitudinal axis A.

Minimizing the relative weakness of the screw of the invention is also made possible by using grooves 10 that are helical since that enables the zones of weakness resulting from the removal of material to provide a groove 10, themselves to be distributed around the longitudinal axis A.

In particularly advantageous manner, the cross-section of the grooves 10 forms an angle that is acute, in any event less than 90°, so as to reduce the amount of material that is removed from the screw, thereby minimizing the extent to which the screw is weakened, but without spoiling its self-tapping properties.

In a preferred variant in the meaning of the invention, in which each groove 10 grows regularly in depth going towards the tip of the screw, the terminal fraction of the groove, i.e. its deepest fraction, is advantageously made through the thickness of the screw body, whereas the beginning portion of each groove 10 is made solely through the thickness of the threads 4A or 7A. This reduces the risk of weakening the screw as a whole.

In a preferred variant, the preparation means 11 are formed by a tooth 11A extending substantially axially.

Although the simplest form of the osteosynthesis screw of the invention may have a single pair only of grooves 10 in the screw head 3 and the distal portion 6, it will be understood that the self-boring and self-tapping properties of the screw can be improved by providing two pairs of grooves 10, or in more preferred manner, three pairs of grooves 10 regularly distributed angularly around the longitudinal axis A and occupying both the proximal and the distal portions of the screw.

In particularly advantageous manner, the two grooves 10 in a given pair, regardless of whether they are longitudinal or helical, can be provided in the proximal and distal portions 2 and 6 of the screw in such a manner as to extend each other.

Naturally, in a variant, the two grooves 10 in a given pair may also be arranged in the proximal and distal portions 2 and 6 of the screw in such a manner as to be offset relative to each other, so that the groove 10 formed in the distal portion 6 of the screw does not extend the groove 10 formed in the proximal portion 2.

Such an offset can be provided with grooves 10 that are longitudinal or helical.

When there are two grooves 10, they are advantageously diametrically opposite, whereas in the preferred case of three grooves 10, they are disposed at 120° intervals about the main axis A of the screw.

Naturally, depending on the size of the screws concerned, it is possible to envisage making four or even more pairs of grooves 10.

The osteosynthesis screw of the invention could also, but not exclusively, be provided with a central bore 12 extending longitudinally so as to form a hollow screw as is well known to the person skilled in the art.

Naturally, when the osteosynthesis screw of the invention is provided with three pairs of grooves 10, the preparation means 11 are constituted simultaneously by a matching number of three teeth 11A disposed that the junctions between the three grooves 10 in the distal portion 6 and the central bore 12.

The technical means implemented in the osteosynthesis and compression screw of the invention first enable the surgeon to use a self-boring and self-tapping osteosynthesis screw which can be put into place in simplified manner, using a small number of tools but without spoiling its strength and compression properties.

After positioning the two bone fragments for joining together relative to each other, the surgeon can merely put the osteosynthesis screw of the invention into position and then begin directly turning that screw since it is simultaneously self-boring and above all self-tapping along its entire length.

There is thus no need to use an auxiliary tool prior to putting the screw into place for the purpose of preparing and tapping not only the distal and intermediate portions of the screw but also the screw head 3.

The present invention thus also provides a novel method of surgery in which the osteosynthesis screw, by virtue of its shape, itself serves, merely on being turned by a screwdriver, to prepare its own housing and its own tapping without it being necessary to perform any prior drilling.

What is claimed is:

1. An osteosynthesis and compression screw for coaptation of small bone fragments, the screw being formed by a single longitudinal body having a longitudinal axis, and comprising:
    a proximal portion formed by a screw head provided with an outside thread, said proximal portion being of diameter greater than the diameter of the remainder of the screw;
    an intermediate portion having no thread; and
    a distal portion provided with an outside thread;
    wherein:
    each of the screw head and the distal portion includes at least one helical groove, firstly extending over the entire axial length of its thread, and secondly being formed through each thread in such a manner to form tapping means; and
    the terminal zone of the distal portion is provided with preparation means for preparing a housing in the bone fragments for receiving the intermediate and distal portions of the screw
    and, wherein said screw is used for coaptation of bone fragments in the step of:
    compressing said bone fragments together by the insertion and turning of said screw.

2. A screw according to claim 1, wherein the obliqueness of each helical groove lies in the range of about 20° to 40°, and is preferably about 25°.

3. A screw according to claim 1, wherein the depth of said groove is constant.

4. A screw according to claim 1, wherein the depth of the grooves each groove varies regularly from the start towards the finish of each groove.

5. A screw according to claim 4, wherein the depth of each groove increases going towards the terminal zone of the screw.

6. A screw according to claim 5, wherein the final portion of each groove penetrates into the thickness of the body of the screw.

7. A screw according to claim 1, wherein the preparation means are formed by a tooth extending substantially axially.

8. A screw according to claim 1, having three grooves regularly angularly spaced apart around the longitudinal axis, and formed in the proximal and distal portions.

9. A screw according to claim 1, the screw being provided with a central longitudinal bore to form a hollow screw.

10. A screw according to claim 8, the screw being provided with a central longitudinal bore to form a hollow screw, and wherein each junction between the grooves and the central bore includes a tooth forming the preparation means.

11. A screw according to claim 1, wherein the obliqueness of each helical groove is about 25°.

12. An osteosynthesis and compression screw for coaptation of small bone fragments, the screw being formed by a single longitudinal body having a longitudinal axis, and comprising:
    a proximal portion formed by a screw head provided with an outside thread, said proximal portion being of diameter greater than the diameter of the remainder of the screw;
    an intermediate portion having no thread; and
    a distal portion provided with an outside thread;
    wherein:
    each of the screw head and the distal portion includes at least one helical groove, firstly extending substantially over the entire axial length of its thread, and secondly being formed through each thread in such a manner to form tapping means; and
    the terminal zone of the distal portion is provided with preparation means for preparing a housing in the bone fragments for receiving the intermediate and distal portions of the screw
    and, wherein said screw is used for coaptation of bone fragments in the step of:
    compressing said bone fragments together by the insertion and turning of said screw.

13. A screw according to claim 12, wherein the obliqueness of each helical groove lies in the range of about 20° to 40°.

14. An osteosynthesis and compression screw for coaptation of small bone fragments, the screw being formed by a single longitudinal body having a longitudinal axis, and comprising:

a proximal portion formed by a screw head provided with an outside thread, said proximal portion being of diameter greater than the diameter of the remainder of the screw;

an intermediate portion having no thread; and a distal portion provided with an outside thread wherein:

each of the screw head and the distal portion includes at least one groove, firstly extending substantially over the entire axial length of its thread, and secondly being formed through each thread in such a manner to form tapping means, wherein the depth of each groove varies regularly from the start towards the finish of each groove; and the terminal zone of the distal portion is provided with preparation means for preparing a housing in the bone fragments for receiving the intermediate and distal portions of the screw;

and, wherein said screw is used for coaptation of bone fragments in the step of:

compressing said bone fragments together by the insertion and turning of said screw.

15. A screw according to claim 14, wherein the depth of each groove increases going towards the terminal zone of the screw.

16. A screw according to claim 14, wherein the final portion of each groove penetrates into the thickness of the body of the screw.

17. A screw according to claim 14, wherein the preparation means are formed by a tooth extending substantially axially.

18. A screw according to claim 14, having three grooves regularly angularly spaced apart around the longitudinal axis, and formed in the proximal and distal portions.

19. A screw according to claim 14, the screw being provided with a central longitudinal bore to form a hollow screw.

* * * * *